United States Patent [19]

Naimon et al.

[11] Patent Number: 4,686,975
[45] Date of Patent: Aug. 18, 1987

[54] ELECTRONIC RESPIRABLE GAS DELIVERY DEVICE

[75] Inventors: Errol J. Naimon, Hopkins; Michael Jackson, Brooklyn Park, both of Minn.

[73] Assignee: Applied Membrane Technology, Inc., Minnetonka, Minn.

[21] Appl. No.: 730,432

[22] Filed: May 3, 1985

[51] Int. Cl.$^4$ ............................................. A61M 16/00
[52] U.S. Cl. ............................ 128/204.23; 128/207.18
[58] Field of Search ...................... 128/204.23, 204.21, 128/204.26, 207.18, 204.24, 204.25

[56] References Cited

U.S. PATENT DOCUMENTS

| | | | |
|---|---|---|---|
| 3,357,428 | 12/1967 | Carlson | 128/204.26 |
| 4,281,651 | 8/1981 | Cox | 128/204.23 |
| 4,401,115 | 8/1983 | Monnier | 128/204.23 |
| 4,461,293 | 7/1984 | Chen | 128/204.23 |
| 4,612,928 | 9/1986 | Tiep et al. | 128/207.18 |

*Primary Examiner*—Henry J. Recla
*Attorney, Agent, or Firm*—Robert W. Doyle; William C. Flynn

[57] ABSTRACT

A supplemental respiratory device is shown that uses electronic components to regulate the flow of a respirable gas to a user, intermittently, on a demmand basis. The present invention, by monitoring small changes in relative airway pressure, caused by the user's inspiratory or expiratory effort, supplies gas only when an inhalation is detected. The present respiratory device can also vary the duration of the gas delivery time to compensate for changes in user breath rate. The invention herein is designed to be compatible with a standard nasal cannula. An electronic apnea detector is shown, and is included in the preferred embodiment of the present invention. In addition, the invention herein, when not used for gas delivery purposes, can be used as a diagnostic device for providing information concerning a user's breathing pattern.

9 Claims, 6 Drawing Figures

ELECTRONIC RESPIRABLE GAS DELIVERY DEVICE

BACKGROUND

1. Field of the Invention

The present invention relates generally to supplemental respiratory devices and, in particular, to those supplemental devices that deliver respirable gas intermittently, based upon user demand.

2. Background of the Invention

Individuals who have a chronic obstructive pulmonary disease, or other form of respiratory insufficiency, often require supplemental oxygen therapy. This therapy involves enriching the air they breathe with enough oxygen to compensate for their reduced respiratory capacity, and thus, to insure they achieve adequate blood-oxygen levels.

Supplemental respiratory systems generally utilize a nasal cannula, connected to a pressurized oxygen source, to deliver the oxygen to the user. Originally, these systems were designed to administer oxygen on a continuous basis, wherein gas was allowed to flow to the user without interruption. However, this delivery mode wasted gas. Oxygen allowed to flow during exhalation or between breaths would dissipate into the ambient air, and thus, would be of no therapeutic value to the user. Various respiratory devices have been developed that are directed towards the goal of reducing this waste, and thereby, reducing the cost of oxygen therapy.

The basic operating principle of these improved devices is to intermittently deliver the gas, on demand, i.e. to supply the gas only during the inspiratory phase of the user's respiratory cycle. Current art respiratory devices utilize fluidic means to sense the negative or positive pressure, relative to atmospheric pressure, that occurs in the user's airway during inspiration and expiration respectively. An example of a fluidic device is seen in U.S. Pat. No. 4,414,982 to Durkan. The Durkan device uses fluidic sensing and gas regulating means to control the flow of gas, from a pressurized gas source, to the user. The Durkan device, however, requires the use of a specialized split nasal cannula that pneumatically isolates its fluidic sensing apparatus from the fluidic shock associated with the onset of each gas delivery. Such split cannulae are more expensive and less available than standard nasal cannulae. A demand regulated respiratory device, as described in U.S. Pat. No. 4,461,293 to Chen, can be used with a standard nasal cannula, and in this regard, is easier and less costly to use than the Durkan device. Also, whereas the Durkan device uses fluidic means for both sensing the user's respiration, and regulating the delivery of oxygen, the Chen device incorporates electronic means to regulate gas delivery. In general, electronic components are smaller and lighter than comparable fluidic devices; thus, electronic components can allow the design of more lightweight and compact, and hence, more portable respiratory devices. Portability is an important consideration, as many individuals who require supplemental oxygen therapy need such respiratory assistance on a long-term basis. Therefore, a portable unit can enhance their mobility, and thus, their quality of life.

Various respiratory devices utilize a fixed delivery approach, whereby the gas is allowed to flow to the user for a set period of time, for each respiratory cycle. However, fixed time respiratory systems can deliver more oxygen than is needed by the user. If the set delivery period exceeds the duration of the user's inhalation, which can occur at the high breath rates common to individuals requiring respiratory supplementation, a portion of the delivered gas will arrive after the inspiratory phase has ended, thereby conferring no therapeutic value to the user.

SUMMARY OF THE INVENTION

The present invention resides in a novel apparatus for delivering a supplemental respirable gas, such as oxygen, to a user intermittently, on a demand-regulated basis. In the preferred embodiment of the present invention, an apneic event detection means is included.

Basically, and in general terms, the present invention includes a means for sensing changes in the user's airway pressure, a means for detecting whether or not such pressure changes indicate the onset of an inspiration, a variable timing means, for regulating the duration of gas flow as a function of increases or decreases in breath rate, and a gas regulating means for regulating the flow of gas from a gas supply source in a manner as determined by the variable timing means.

The pressure sensing means of the device herein is used for monitoring changes in pressure occurring at or near the point of delivery of gas to the user. This pressure information is communicated from a nasal cannula to the sensing means, through a hose or other suitable pneumatic conduit. The sensing means produces a first electrical signal proportional in strength to the negative pressure caused by the individual's inhalation. This first signal is then sent to an inspiration detection means. The function of the inspiration detection means is to produce a second electrical signal only when the first signal is of sufficient strength, thus indicating the onset of an inspiration. The second signal, produced by the inspiration detection means, is then sent to a variable timing means. The timing means, when activated by the second signal, initiates a timing cycle during which a third electrical signal is sent to a gas regulating means. The regulating means, when energized by the third signal, allows gas to flow to the user for the duration of the timing cycle. The gas is delivered to the user through a hose, or other suitable pneumatic conduit, connecting the regulating means to the nasal cannula. Although, in the preferred embodiment of the present invention the delivery of gas is based upon the detection of the start of inspiration, through suitable adjustment of the inspiration detection means, the present invention can be configured to deliver gas based upon the detection of the end of expiration.

In the preferred embodiment of the present invention, the timing means is variable, which means the duration of its timing cycle can be adjusted to compensate for changes in user breath rate. Fixed time delivery systems allow the same volume of gas to flow to the user for each cycle, regardless of the breath rate. The present invention can shorten or lengthen the duration of the timing cycle in response to increases and decreases, respectively, in user breath rate. This self-adjusting ability is particularly valuable at the higher breath rates, above twenty breaths per minute, common among individuals requiring supplemental oxygen therapy. At these higher breath rates, fixed time delivery systems tend to oversupply oxygen by delivering gas for a period of time that exceeds the duration of the inspiratory phase. This oversupplied portion of gas is of no therapeutic value to the user. In the present invention, adjustment of the timing cycle is accomplished with an inspiration frequency detection means. The third electrical signal, generated by the timing circuit, is also sent to the frequency detection means. This frequency detection means monitors the number of such signals over time, which information correlates directly with the breath rate. Through a second connection with the timing means, a fourth electrical signal, generated by the frequency detection means, is fed back to the timing means, causing the appropriate timing cycle adjustment. Thus, the present invention, based upon a breath-by-breath analysis, decreases the duration of the timing cycle if the breath rate increases, and increases the duration of the timing cycle if the breath rate decreases. As a result, the present device can more accurately supply gas based upon user demand, allowing increased efficiency of oxygen use, without compromising the user's health care needs.

The present invention has been designed for use with a single standard nasal cannula. However, use of a standard cannula results in the pneumatic communication of the pressurized gas supply with the sensing means. A pressure pulse associated with each delivery of gas can cause the production of a false inspiration signal, hence causing the delivery of unneeded gas. Thus, the variable timing means of the present invention includes delay circuits that allow the timing means to "suppress" such false signals.

The present invention can be operated effectively on a battery power supply, and can be made lightweight and compact due to the utilization of electronic components. Therefore, the present respiratory device can be designed to be easily portable.

In the preferred embodiment of the present invention, an electronic apneic event detection means is included. As previously described, initiation of a timing cycle, hence production of a third electrical signal, is evidence that the user has inspired, thus normal breathing is indicated by a continual train of such third electrical timing cycle signals. The apneic detection means is designed to await the arrival of these third signals. If the time lapse from the arrival of the last such signal exceeds a predetermined length, cessation of breathing is indicated. An electrical signal is then generated by the apneic detection means that can be used to activate or initiate activation of an alarm system.

The present invention can also be used to provide diagnostic information concerning the user's breathing pattern when interfaced with various display or recording devices.

Accordingly, it is an object of the present invention to deliver a respirable gas to a user, intermittently, on a demand regulated basis.

It is further an object of the present invention to deliver the respirable gas only during the user's inspiratory phase.

It is further an object of the present invention to adjust the amount of gas delivered during each inhalation, in a manner related to the user's breath rate.

It is further an object of the present invention to be compatible with a standard nasal cannula.

It is further an object of the present invention that it be compact, lightweight, and portable.

It is further an object of the present invention that it be able to detect an apneic event.

It is further an object of the present invention to be able to provide a diagnostic information concerning the user's breathing pattern.

These and further objects and advantages of the present invention will become clearer in light of the following detailed description of the preferred embodiment.

BRIEF DESCRIPTION OF THE DRAWINGS

The illustrative embodiments of the present invention may best be described by reference to the accompanying drawings where.

DETAILED DESCRIPTION OF THE PREFERRED EMBODIMENT

Figures 1, 2:
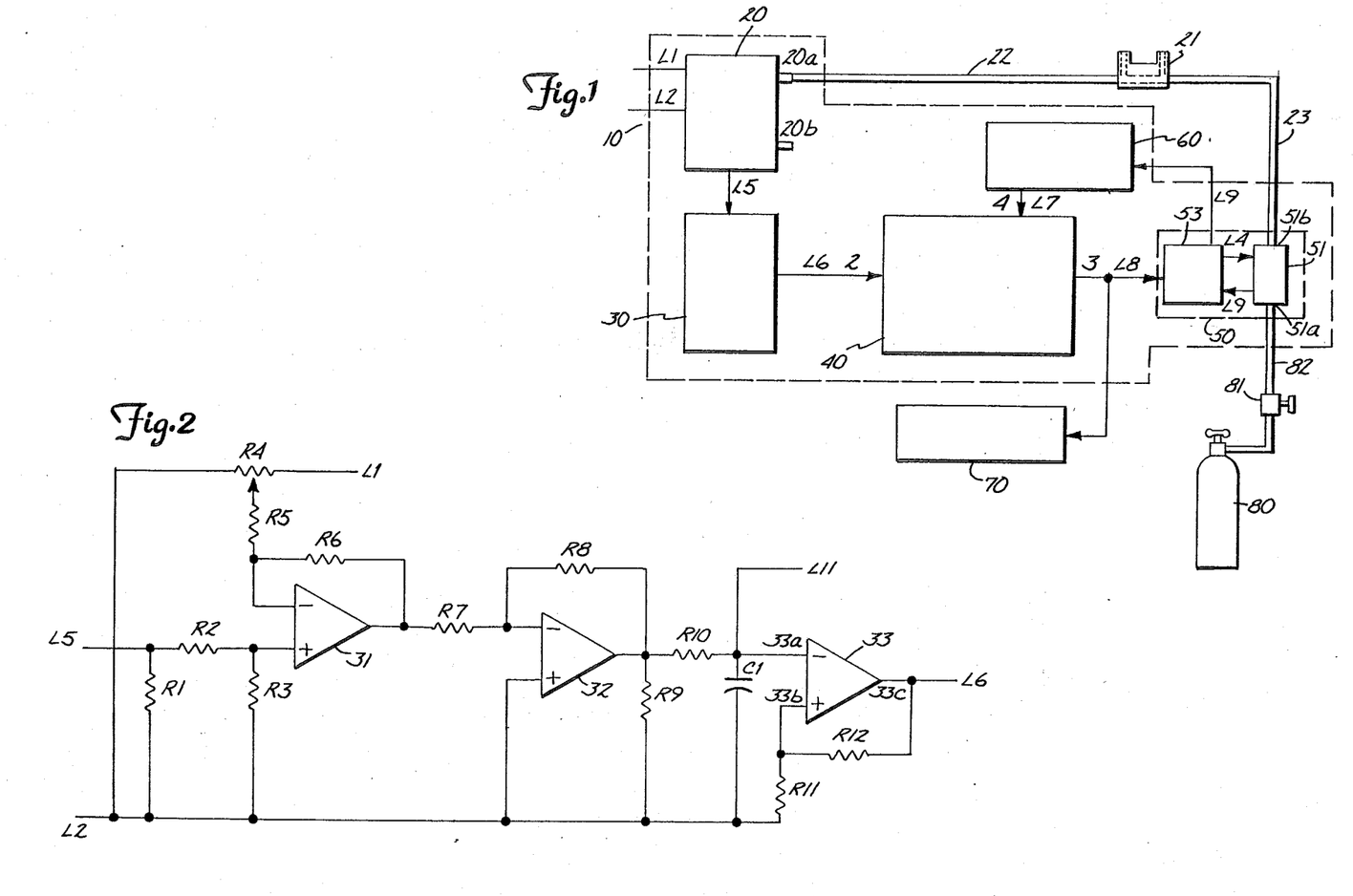
FIG. 1 shows a block diagram illustration of the present invention.
FIG. 2 shows a schematic representation of the inspiration detection means of the present invention.

The electronic respirable gas delivery device of the present invention is seen in block diagram form in FIG. 1, and generally designated 10.

Respirable gas delivery device 10 includes, as seen in FIG. 1, pressure sensing means 20, which serves to convert negative or positive changes in user airway pressure, relative to atmospheric pressure, to a first electrical signal, which signal is proportional in strength to the degree of the positive or negative change. A positive or negative pressure change corresponds to exhalation and inhalation respectively. Sensing means 20 is connected to nasal cannula 21 by first pneumatic conduit 22, as seen in FIG. 1 via input port 20a, input port 20b of sensing means 20 is open to atmospheric pressure. Conduit 22, which consists of standard nasal cannula tubing, serves to communicate the changes in the user's airway pressure from nasal cannula 21 to sensing means 20. Thus, the electrical signals produced by sensing means 20 serve to indicate if an inhalation or exhalation is occurring and provide the basis for determining the appropriate timing of gas delivery. In the present invention, sensing means 20 consists of a differential pressure transducer such as model 163PC01D36, manufactured by Micro Switch, Freeport, Ill. The quiescent output of this transducer is approximately +3.5 volts DC (VDC) with a +8 VDC excitation. Its properties have been optimized for +8 VDC excitation. Sensitivity of the transducer is approximately 0.5 VDC per inch of water pressure differential.

To facilitate the description of the present invention, the notation "LX" is used to denote an electrical line where "X" is a reference designation. For example, with reference to FIG. 1, sensing means 20 includes a line L1 connected to a positive DC voltage supply (not shown) and a line L2 connected to a common DC reference potential supply (also not shown). The potential difference across L1 and L2 is 8 volts DC (VDC). Similarly, with reference to FIG. 5, a line L3 is connected to a negative DC voltage supply (not shown) and lines L1 and L2, as previously described, are also shown. The potential difference across L2 and L3 is 8 VDC. As a last example, with reference to FIG. 4, respirable gas delivery means 50 includes a line L4 connected to a positive DC voltage supply (not shown). The potential difference across L4 and L2 is 10–12 VDC.

Inspiration detection means 30 is connected to sensing means 20 by line L5, as seen in FIG. 1, and detection mean 30 serves to determine if an inspiration is occurring. The basic operation of inspiration detection means 30 involves comparing the voltage output produced by sensing means 20, associated with the negative pressure caused by inhalation, with a certain pre-set reference voltage. When the voltage output of sensing means 20 exceeds this pre-set value, an inspiration is indicated and a second electrical signal will be produced. It is likewise possible, through suitable adjustment of inspiration detection means 30, to trigger the delivery of gas based upon the detection of the end of exhalation, as will be described in more detail at a later point.

Referring to the detailed schematic representation of inspiration detection means 30 in FIG. 2, before the voltage change produced by sensing means 20 can be compared with the reference voltage, the signal output of sensing means 20 must first be conditioned. Conditioning of the first electrical signal output of sensing means 20 is accomplished by operational amplifiers 31 and 32. Amplifier 31 and resistors R2, R3, R5, and R6 form a unity gain difference amplifier. Amplifier 31 translates the quiescent output voltage of sensing means 20, driving load resistor R1, to near ground potential L1 via suitable adjustment of variable potential resistor R4. Amplifier 32 and resistors R7 and R8, as seen in FIG. 2, invert and amplify (X16) the translated output voltage of sensing means 20 and produce an effective full-scale output of +/−0.5 inch of water pressure differential. Resistor R10 and capacitor C1, as seen in FIG. 2, form a low-pass filter with a cutoff frequency of approximately 16 Hz to eliminate audio frequency noise transmitted by sensing means 20. The output of sensing means 20 is now in a condition to be compared with the pre-set reference voltage generated by voltage divider resistors R11 and R12. Comparator 33, as seen in FIG. 2, normally holds its output 33c in positive saturation near the positive supply potential of L1, provided that the voltage at inverting input 33a of amplifier 33 is lower than the reference voltage at non-inverting input 33b of amplifier 33. Output 33c of amplifier 33 changes state, drops into negative saturation near the negative supply potential of L3, when the voltage of the conditioned signal of sensing means 20 at inverting input 33a rises above the voltage of non-inverting input 33b, as would occur from any minimal inspiratory effort. The resulting output state transition of comparator 33 provides the second electrical signal which permits the flow of respirable gas to commence. As was mentioned previously, it is also possible in the present invention to trigger gas delivery based upon the detection of the end of each exhalation. This positive pressure based delivery mode is accomplished by adjusting variable potential resistor R4 so that the quiescent output potential of amplifier 32 is just higher, rather than just lower as described earlier, than the reference voltage at non-inverting input 33b of amplifier 33. Thus, when gas delivery is based upon the sensing of the end of exhalation, the second signal is produced when the strength of the first signal falls below a certain pre-set reference voltage, i.e., when the first signal is not of sufficient strength to indicate exhalation. This adjustment must be done when output 33c of amplifier 33 is at the positive supply potential L1, since resistors R11 and R12 create about 150 mV of hysteresis upon output state transitions of comparator 33. This hysteresis is necessary to stabilize the output state transitions of comparator 33 due to the extremely slow, 0.1 Hz–1.0 Hz voltage signal at input 33a. The form of amplifiers 31, 32, and 33 have not been specified and are not critical to the invention. Power supply connections to these amplifiers are established by connecting the positive power supply terminal of each amplifier to the positive supply voltage L1 and the negative supply terminal of each amplifier to the negative supply voltage L3. Those skilled in the art will recognize that in the interest of space and power efficiency, a low-power quad operational amplifier integrated circuit such as the type LM324, manufactured by National Semiconductor, may be used, three amplifiers serving the function of amplifiers 31, 32, and 33, and a fourth amplifier is available for later use.

Figure 3:
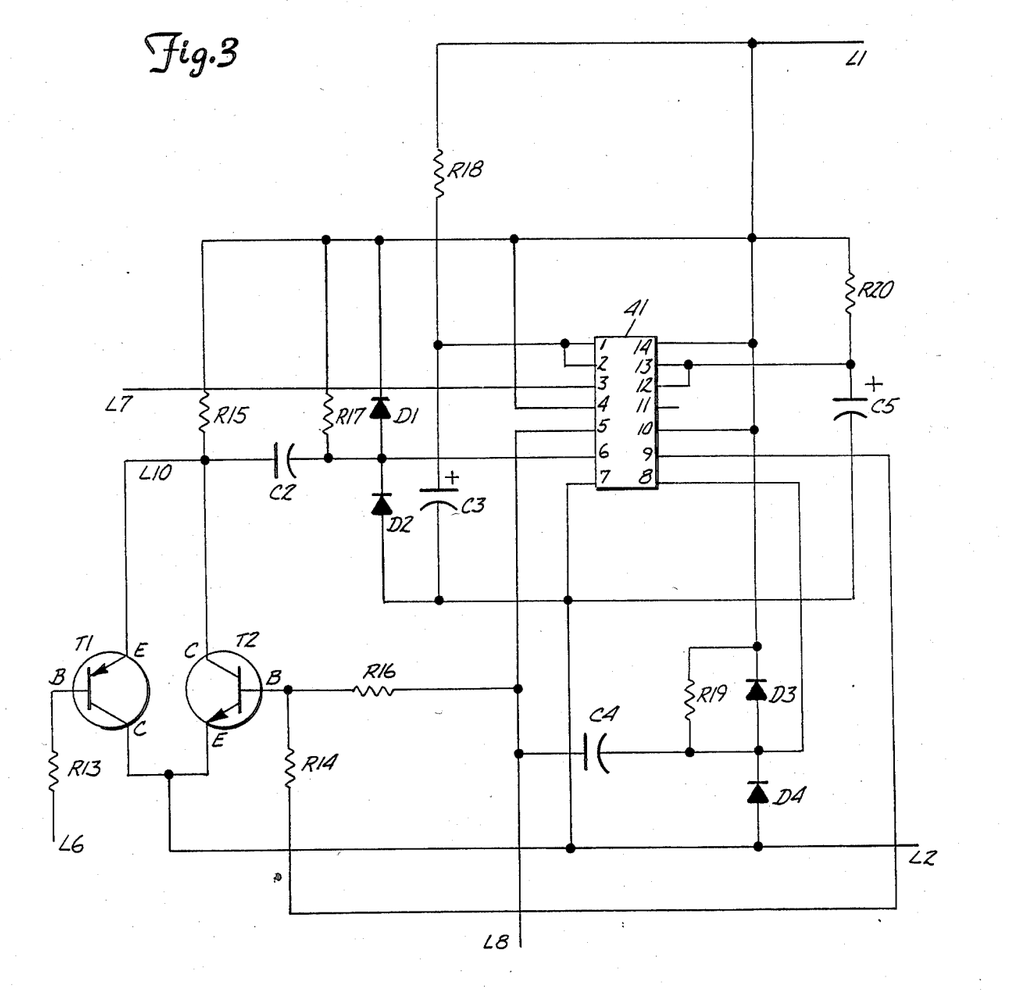
FIG. 3 shows a schematic representation of the electronic variable timing means of the present invention.

The duration of time that gas is delivered to the user for any one breath and the third electrical signal that triggers the actual release of gas to the user is controlled by electronic variable timing means 40, connected to inspiration detection means 30, as seen in FIG. 1 by line 6. As the second electrical signal generated by inspiration detection means 30 requires additional controlled buffering to transform it into a signal suitable for use in subsequent delicate timing stages. The output of comparator 33 which swings from near the positive potential of L1 to near the negative potential of L3 approximately +/−8 VDC, is buffered by normally-off PNP switching transistor T1, such as the type available from National Semiconductor as part 2N3906, and resistors R13 and R15, and is connected to buffer T1 by line L6, as seen in the detailed schematic of variable timing means 40 in FIG. 3. Normally the output 33c of comparator 33 is near the positive supply potential of L1, shutting off transistor T1 through base resistor R13, pulling the voltage at the emitter of transistor T1 up to the positive supply potential of L1 through resistor R15. At the instant of inspiration, the output 33c of comparator 33 drops to near the negative supply potential of L3, driving transistor T1 into saturation through resistor R13, causing current to flow through resistor R15 dropping the potential at the emitter of transistor T1 to near ground potential L2. In this manner, the voltage at the emitter of transistor T1 "follows" the voltage at output 33c of comparator 33. However, instead of swinging from near the positive supply potential L1 to near the negative supply potential L3, the voltage at the emitter of transistor T1 swings only from near the positive supply potential L1 to ground potential L2. The negative going and positive going transitions at the emitter of transistor T1 are differentiated by a resistor-capacitor network composed of resistor R17 and and capacitor C2, as seen in FIG. 3, which network passes only the transistion "edges". The signal "edges" passed by the resistor-capacitor network of resistor R17 and capacitor C2 are used to trigger CMOS integrated circuit dual timer 41, such as the type ICM7556, manufactured by Intersil. Timer 41, when so tripped, produces a third electrical signal for a period of time which determines the length of time respirable gas flows to the user. If timer 41 were not configured as an edge-triggered device and the timing cycle ended before the user had stopped inhaling sufficiently to cause an output from comparator 33, timer 41 could be falsely triggered, causing the delivery of unneeded gas to the user. Clamp diodes (both IN914) D1 and D2 limit the voltage excursions of pulses coupled by capacitor C2 to safe levels, i.e., 300 mv above the positive supply potential of L1 and 300 mv below the floating reference ground potential L2. As regards timer 41 and its associated circuitry, most of this circuitry functions in a logic sense under control of analog circuitry either already described or described below. The clarity of the disclosure is thus enhanced by the introduction of language indicative of a logic environment. Hereinafter, unless otherwise noted, reference to a logic "true" condition will be synonymous with the occurrence of a voltage substantially equivalent to positive supply potential L1; conversely, reference to a logic "false" condition will be synonymous with the occurrence of a voltage substantially equivalent to floating reference ground potential L2.

Figures 4, 5:
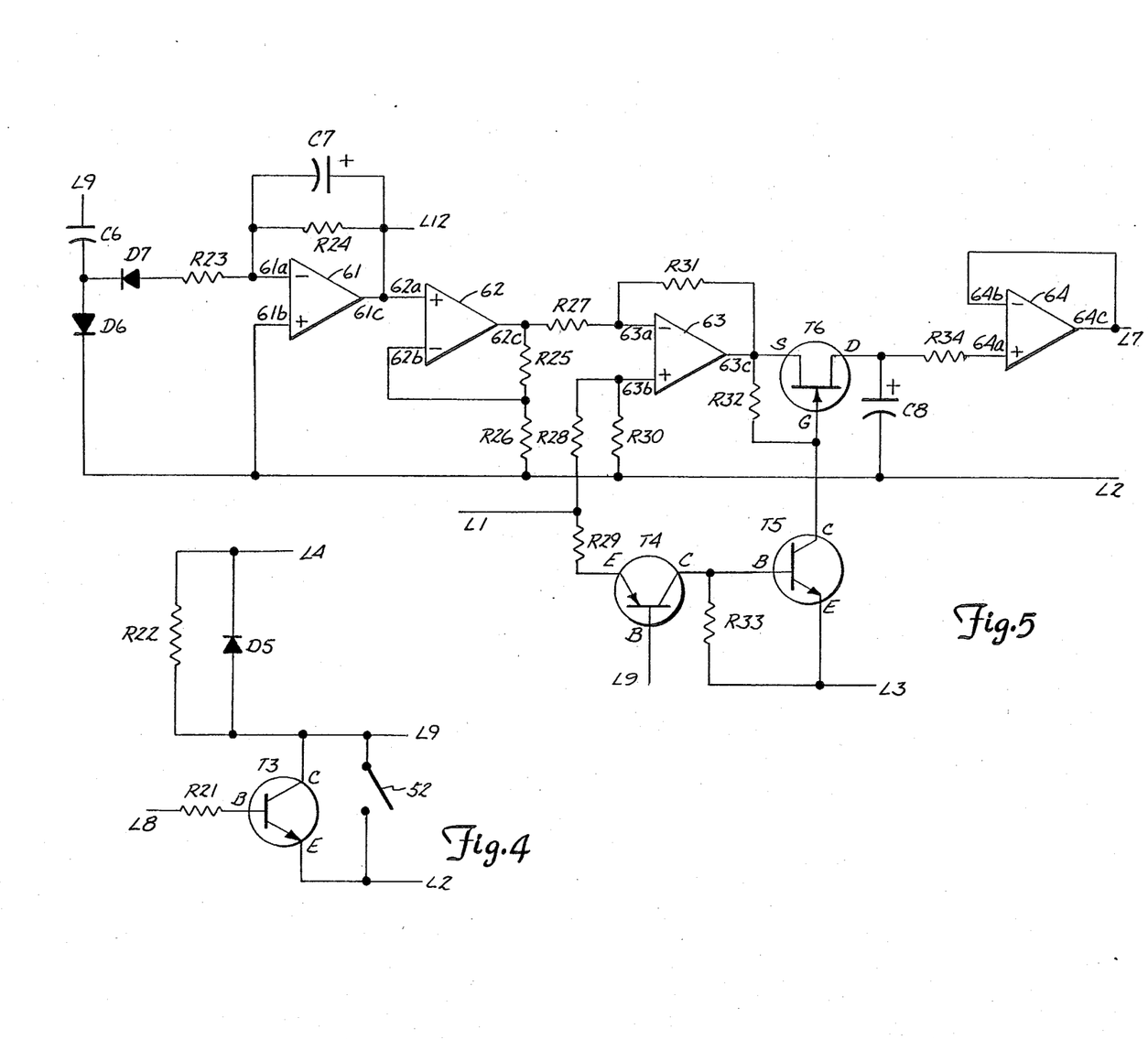
FIG. 4 shows a schematic representation of the interface circuit of the respirable gas delivery means of the present invention.
FIG. 5 shows a schematic representation of the inspiration frequency detection means of the present invention.

Exclusive of power supply connections to L1 and L2, pins 1 through 6 of timer 41, resistor R18 and capacitor C3, as seen in FIG. 3, form a voltage controlled, monostable pulse-width modulator. Upon inspiration, the buffered negative going edge of comparator 33 travels along line L10, seen in FIG. 3, to trigger input pin 6 of timer 41, also seen in FIG. 3, producing a false at pin 6 of timer 41. As a result, output pin 5 of timer 41, quiescently false, goes true, and initiates a timing cycle via resistor R18 and capacitor C3, seen in FIG. 3. The output true of pin 5 of timer 41 causes a third electrical signal to be sent along line L8, seen in FIG. 1, to respirable gas delivery means 50, seen in FIG. 1. The operation of delivery means 50, consisting of respirable gas interface circuit 53 and solenoid valve 51, can be better understood by reference to interface 53 and its detailed schematic, as seen in FIG. 4. The true from pin 5 of timer 41, seen in FIG. 3, travels along line L8 to normally-off NPN switching transistor T3, such as the type available from National Semiconductor as part 2N2222, seen in FIG. 4. Referring to FIG. 4, transistor T3 is then driven into saturation through base resistor R21, causing T3 to conduct, energizing the coil of 2-way normally-closed electric solenoid valve 51, such as the type number M3E1-12V, as manufactured by Humphrey Products, Kalamazoo, Mich. Valve 51, as seen in FIG. 1, has pneumatic input 51a and pneumatic output 51b, isolated when the coil of valve 51 is de-energized and the orifice of valve 51 is closed, but connected pneumatically when the coil of valve 51 is energized, the orifice of valve 51 then being opened. When so energized and opened, valve 51 allows respirable gas to flow from respirable gas source 80, such as a compressed oxygen cylinder, through a flow regulating valve 81, through interconnecting pneumatic conduit 82, through valve 51, and through pneumatic conduit 23 and nasal cannula 21 to the user. Since the coil of valve 51 remains energized for the duration of the true signal at pin 5 of timer 41, seen in FIG. 3, respirable gas continues to flow for the duration of the timing cycle. At the conclusion of the timing cycle, pin 5 of timer 41 goes false, shutting off transistor T3, seen in FIG. 4, blocking current flow through the coil of valve 51, causing de-energization of the coil of valve 51 and closing the orifice of valve 51, once again isolating pneumatic input port 51a and pneumatic output port 51b, seen in FIG. 1, blocking the flow of respirable gas to the user.

Flow regulating valve 81 and pneumatic conduit 82 must be matched to source 80 to provide proper respirable gas flow to the user. With flow regulating valve 81 placed intermediate solenoid valve 51 and source 80, conduit 82 pressurizes when solenoid valve 51 is closed, the equilibrium pressure dependent on the nature of flow regulating valve 81 and source 80. For example, if a compressed oxygen gas cylinder is employed as source 80, and is used with a fixed orifice, variable pressure flow regulating valve 81, such as the type available from Veriflo Corp., Richmond, Calif., as part 707 870 FG 5, conduit 82 will pressurize to approximately 64 psig when valve 51 is closed and the dial setting on flow regulating valve 81 is 2 liters per minute. When valve 51 opens, the gas stored in conduit 82 abruptly escapes through valve 51, second conduit 23, and nasal cannula 21 to the user, at a rate limited by the combined flow resistance of these elements, in substantial excess of the rate indicated by the dial setting on flow regulating valve 81. As valve 51 remains open, conduit 82 depressurizes to a lower pressure at some intermediate level between atmosphere and 64 psig as required to drive the rate at the dial setting of flow regulating valve 81 through the combined flow resistances of second conduit 82, valve 51, conduit 23, and nasal cannula 21. This method of delivery provides a greater volume of respirable gas to the user during the effective early portion of inspiration immediately after valve 51 opens, a technique well established in the prior art. Conduit 82 must be properly sized, however, so that the greater volume of gas that is applied at the onset of inspiration does not include a substantial portion that is not inspired and therefore wasted, as well as being sized for complete pressurization of said conduit during the time that valve 51 remains closed, regardless of breath frequency up to a limit of approximately 60 breaths per minute for an adult.

In accordance with the above operating principles, conduit 82 should have a volume of 2.5 cc or less when applied to source 80 and flow regulating valve 81 described above. If source 80 were a cryogenic liquid oxygen system such as the type available from Puritan-Bennett Co., Lenexa, Kans., as model "Companion" with built-in flow regulating valve 81 of a fixed pressure (21 psig) variable-orifice type, conduit 82 should have a volume of 6.0 cc or less. During the time that respirable gas is flowing from valve 51 through pneumatic conduit 23 to nasal cannula 21 seen in FIG. 1, due to the restriction of nasal cannula 21, pneumatic conduits 22 and 23 pressurize beyond the full scale of the signal conditioned pressure signal of sensing means 20, hence airway inspiratory and expiratory information during this time is lost. The saturation of the detector, however, may be used to monitor the flow of respirable gas. Should the nasal cannula 21 be disconnected, the gas source 80 be exhausted, or the respirable gas otherwise not flow, pneumatic conduits 22, 23 will not pressurize and thereby fail to drive the pressure sensing means 20 to full scale. The failure of the pressure sensing means 20 to reach full scale is usable to detect a failure of the device to provide respirable gas to the user. As seen in FIG. 4, diode D5 (1N4001) protects transistor T3 from the inductive kickback caused by the de-energiziation of the coil of valve 51. Pull-up resistor R22, seen in FIG. 4, prevents the voltage at the collector of transistor T3 from floating should valve 51 become disconnected. If desired, normally-open SPST switch 52, seen in FIG. 4, may be closed, grounding the collector of transistor T3, energizing the coil of valve 51, causing valve 51 to open, allowing respirable gas to flow continuously.

Passage of the trigger pulses to timer 41 may be defeated by a suppressing means consisting, in part, of normally-off NPN switching transistor T2, such as type 2N2222, seen in FIG. 3, in which the base of transistor T2 is driven through a "wired-or" resistors R14 and R16, also seen in FIG. 3. As seen in FIG. 3, the collector of transistor T2 is common to the emitter of transistor T1; hence, if transistor T2 is driven into saturation by a true input to either base resistors R14 or R16, T2 will conduct causing current to flow through resistor R15 producing a false at the emitter of transistor T1. This action essentially suppresses passage of inspiration detection pulses originating at output 33c of comparator 33, seen in FIG. 2, through buffer amplifier T1, seen in FIG. 3, since the emitter voltage of transistor T1 no longer follows the output of comparator 33. This circuitry is necessitated in order to prevent false triggering, triggering by other than inspiration, of timer 41 caused by the pneumatic input imparted to sensing means 20 each time gas is delivered to the user, as sensing means 20 is in pneumatic communication with pneumatic line 23, through nasal cannula 21 and first pneumatic conduit 22, as seen in FIG. 1. The suppressing means of the present invention is further comprised of a second timer section of CMOS dual timer 41 utilizing pins 8, 9, 10, 12, and 13, exclusive of power supply connection to L1 and L2, resistors R19 and R20, capacitors C4 and C5, and input clamp diodes D3 and D4 (both 1N914). As seen in more detail in FIG. 3, output pin 5 of timer 41 is capacitively coupled via capacitor C4, pull-up resistor R19, and clamp input protection diodes D3 and D4 to trigger input pin 8 of timer 41, causing pin 9 of timer 41 to go true for a fixed time duration of approximately 0.25 seconds, as dictated by the RC time constant of resistor R20 and capacitor C5. During this time period, the output true at pin 9 of timer 41 drives transistor T2 into saturation, effectively disabling passage of comparator 33 pulses to input trigger pin 6 of timer 41. This action of the suppressing means prevents timer 41 from retriggering after cannula 21 and conduits 22 and 23 depressurize, assuming that either the user is still inhaling, or that the sensing diaphragm of sensing mean 20 overshoots its neutral position owing to its own inertia, thereby insuring that timer 41 delivers gas for only one timing period per breath, at the onset of inspiration.

The action of said suppressing means is described in detail as follows: When respirable gas is flowing, transistor T2, as previously described and as seen in FIG. 3, is driven into saturation, causing T2 to conduct, holding its collector false, preventing passage of signals from comparator 33 to timer 41 along line L10. This action appears redundant as timer 41 cannot be retriggered during its timing cycle; however, it is desirable to hold the common connection of the emitter of transistor T1 and the collector of transistor T2, as seen in FIG. 3, false during the timing cycle to prevent any possibility of re-triggering timer 41 immediately after its timing cycle has been completed. Preventing this re-triggering is necessary, as the collector of transistor T2 is held false for a short period of time immediately following the conclusion of the timer 41 timing cycle, as previously described. If the collector of transistor T2 was permitted to go true during the timing cycle of timer 41, a negative-going edge would be created when delay timer output pin 9 of timer 41, goes true, approximately 300–600 ns after pin 5 of timer 41 goes false, spontaneously re-triggering timer 41. This improper action would be self-sustaining as well. The propagation delay of 300–600 ns, which varies with respect to the manufacturer of timer 41, between the output true of pins 5 and 9 of timer 41, would cause a spike at the collector of transistor T2 were it not for the relatively large RC time constant of resistor R15 and capacitor C2.

The net effect of the action of transistors T1 and T2 with base drive resistors R13, R14, and R16, and output at the common connection of the emitter and collector of transistors T1 and T2 respectively, is to function as a 3-input NOR gate. Logic "false" levels are at ground supply potential L2, except for the input at base resistor R13 which is "false" at the positive supply potential L1. Logic "true" levels are at the positive supply potential L1, except for the input at base resistor R13 which is "true" at the negative supply potential L3. The logic "true" level at the base resistor R13 input along L6 corresponds to the detection of inspiration by comparator 33, as previously described, and represents the application of inverted logic (i.e., logic "true" corresponds to a low potential; logic "false" corresponds to a higher potential).

In the present invention the length of the timing cycle of output pin 5 of timer 41, hence the duration of time respirable gas is allowed to flow to the user, is automatically varied so that the time of gas delivery decreases as the user's breath rate increases, and increases as the user's breath rate decreases. This automatic timing cycle adjustment is accomplished by inspiration frequency detection means 60, connected to electronically variable timing means 40 and gas delivery means 50, by lines L7, L8, and L9, as seen in FIG. 1, in a closed loop fashion.

The operation of detection means 60 can be understood by referring to the detailed schematic of detection means 60 as contained in FIG. 5. Amplifier 61, resistors R23 and R24, diodes D6 and D7 (both 1N914), and capacitors C6 and C7, as seen in FIG. 5, form a frequency-to-voltage converter, of a form well known to those skilled in the art, with an output at output 61c of amplifier 61, which voltage increases with increasing frequency of breath. Coupling of inspiratory occurrence to the converter originates from line L9 from valve driver transistor T3, as seen in FIG. 4, which provides a negative-going pulse at its collector each time output of timer 41, as seen in FIG. 3, goes true. This falling edge signal occurs once per breath, during periods of steady breath rate, and at most once per breath during periods of rapidly changing breath rate, as the transient response of converter amplifier 61 output 61c is damped. Amplifier 62 and resistors R25 and R26, as seen in FIG. 5, form a non-inverting amplifier with a gain of 15, which scales the output of converter amplifier 61 upward. Amplifier 63 and resistors R27, R28, R30, and R31, as seen in FIG. 5, form a unity-gain difference amplifier with an output that decreases with increasing frequency of breath. Output 63c of amplifier 63, as seen in FIG. 5, is captured by subsequent stages and becomes the fourth electrical signal, a modulating voltage for output timer 41, which regulates the delivery period of the respirable gas.

Buffering for the on-time modulation voltage at outtput 63c of amplifier 63 is provided by a unity-gain sample and hold (S/H) amplifier, of a form well known to those skilled in the art, which consists of resistors R29, R32, R33, and R34, transistors T4, T5, and T6, hold capacitor C8, and buffer amplifier 64, as seen in FIG. 5. N-channel FET T6, such as type 2N3819, manufactured by National Semiconductor, as seen in FIG. 5, is configured as an analog switch and controlled by the voltage at the collector of NPN switching transistor T5, such as type 2N2222. The control input to the entire S/H amplifier network originating at pin 5 of timer 41, is applied at the base of PNP switching transistor T4, such as type 2N3906, seen in FIG. 5. This signal originates from pin 5 of timer 41.

The control voltage at output 64c of amplifier 64 applied to pin 3 of timer 41 along L7, must be held constant during the timing cycle of timer 41, for reliable operation of the device herein. During the timing cycle, the voltage at the base of transistor T4 is near ground potential L2, which is a logic "false" input which controls the S/H network to hold the input voltage from the output 63c of amplifier 63 on hold capacitor C8. Due to the high impedance of amplifier 64, no current flows through transistor 34 and hence, the voltage held on C8 appears also at non-inverting input 64a of amplifier 64. The voltage follower configuration of amplifier 64 causes the voltage at 64a to appear also at inverting input 64b and output 64c of amplifier 64. Unity gain follower 64 thereby buffers capacitor C8 from any possible loading by timer 41. Resistor R34 limits the discharge current from capacitor C8 into amplifier 64 when power is removed. For the time during which timer 41 is not undergoing a timing cycle, thus pin 5 of timer 41 is false, the voltage at the base of transistor T4 is at the positive supply potential L4, a logic "true" input which controls the S/H network to sample or track the voltage at output 63c of amplifier 63. The output voltage of the S/H network is the fourth electrical signal which is used to control the length of time of respirable gas delivery. The form of amplifiers 61, 62, 63, and 64 have not been specified and are not critical to the invention; however, those skilled in the art will recognize that a ground sensing low power quad operational amplifier IC, such as the type LM324, manufactured by National Semiconductor, may be used in the interest of space and power conservation in accordance with the object of portability. Power supply connections to these amplifiers are made by connecting the positive supply terminal to positive voltage supply L1 and by connecting the negative supply terminal to ground potential L2, provided that ground sensing amplifiers are employed; otherwise, the negative supply terminal should be connected to negative voltage supply L3.

The duration of an output true at pin 5 of timer 41, seen in FIG. 3, is the total time per breath the respirable gas is allowed to flow. This time period is modulated by the application of the control voltage of output 64c of amplifier 64, seen in FIG. 5, to pin 3 of timer 41, seen in FIG. 3. This voltage output from the S/H network, as previously described, decreases linearly with increasing breath rate. The duration of respirable gas flow decreases as the logarithm of the reciprocal of the difference between the positive supply voltage L1 and the control voltage L7. The net result is that the ratio of gas flow time to total time between breaths remains substantially constant over a wide variation in breath rate, in particular for the 12–40 breath-per-minute range. This ratio may be selected by suitable adjustment of the gain of amplifier 62, seen in FIG. 5, and of the RC time constant of resistor R18 and capacitor C3, also seen in FIG. 3.

The preferred operation of the present invention can now be appreciated. As seen in FIG. 1, pressure sensing means 20 is connected to cannula 21 through first pneumatic conduit 22. At the start of an inspiration, the negative airway pressure changes caused thereby are communicated to sensing means 20 from nasal cannula 21 through first pneumatic conduit 22. The first electrical signal produced by sensing means 20 is interpreted by inspiration detection means 30, seen in FIG. 1, which detection means produces a second electrical signal, if the change in airway pressure is of a sufficient value, thus indicating the onset of an inspiration. The second signal produced by detection means 30 is then sent to electronic variable timing means 40, which variable timing means initiates a timing cycle during which a third electrical signal is sent to gas delivery means 50, which delivery means causes respirable gas to flow to the user for the duration of the timing signal. Variable timing means 40 includes circuitry to block the false initiation of further timing cycles. Inspiration frequency detection means 60, as seen in FIG. 1 is connected to line L7 and to variable timing means 40. Changes in user breath rate, as monitored by detection means 60, from line L9, are fed back into variable timing means 40 by a fourth electrical signal, causing appropriate adjustments in the length of the timing cycle. Thus, if user breath rate increases, the duration of time of gas delivery is shortened, and conversely, as user breath rate decreases, the length of time of gas delivery is increased.

Figure 6:
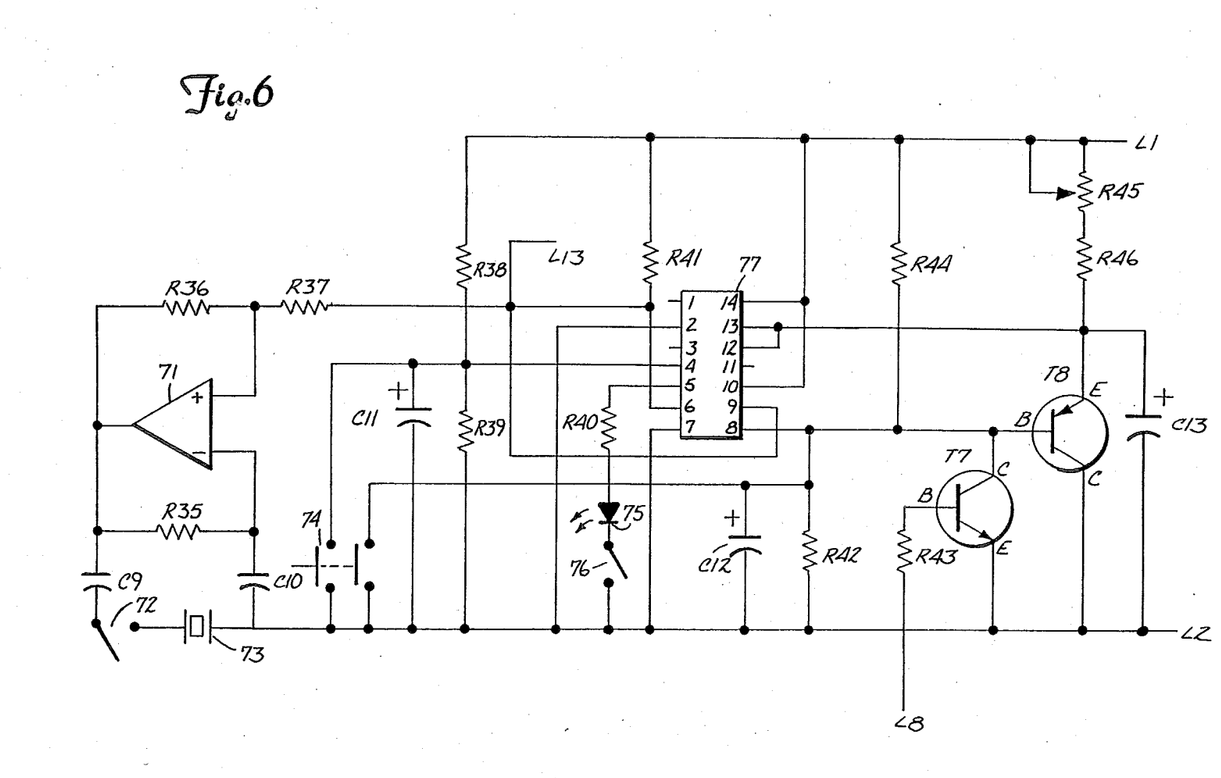
FIG. 6 shows a schematic representation of the apneic event detection means of the present invention.

The present invention also includes apneic event detection means 70 used to detect a cessation of breathing or improper cannula placement. As seen in FIG. 1, apneic event detection means 70 is connected to line L8, which line also connects variable timing means 40 to respirable gas delivery means 50. As described previously, the third electrical signal produced by timing means 40 activates delivery means 50, enabling delivery of gas to the user. Therefore, a continued train of such third electrical signals indicates that the user is breathing. Through connection to line L8, detection means 70 is designed to await the arrival of each such third electrical signal pulse, whereby if the time lapse from the arrival of the last such electrical pulse exceeds a predetermined length, the occurrence of an apneic event is indicated, and detection means 70 will trigger an alarm. The operation of detection means 70 can be better understood by reference to the schematic of detection means 70, as seen in FIG. 6. The basic missing-pulse detection circuitry of detection means 70 can be seen in FIG. 6, and consists of resistors R41, R42, R43, R44, R45, and R46, transistors T7 (2N2222) and T8 (2N3906), capacitors C12 and C13, and CMOS dual timer IC 77, such as the type ICM7556, as available from Intersil. Connections for missing-pulse detection are made to pins 8, 9, 10, 12, and 13 of timer chip 77, exclusive of power supply connections, as indicated on FIG. 6. Output pin 9 of timer 77 is normally true, via pull-up resistor R41, but when the current through user-adjustable variable resistor R45 and R46 accumulates charge on capacitor C13, bringing the voltage of capacitor C13 to $\frac{2}{3}$ of the positive supply voltage L1, output pin 9 of timer 77 goes false. It is the negative-going transition of output pin 9 of timer 77 that is the fifth electrical signal along line L13, which signal indicates the detection of an apneic event. In normal operation, e.g. wherein the user continues to respire, this control signal is not produced as detection means 70 is continually reset by timer 41 along line L8, seen in FIG. 3, wherein output pin 5 of timer 41 drives normally-off NPN and PNP switching transistors T7 and T8 into saturation through base resistor R43. This action causes T7 and T8 to conduct draining timing capacitor C13 of charge, thus preventing the voltage of capacitor C13 from reaching the necessary voltage threshold to cause output pin 9 of timer 77 to go false. Variable resistor R45 provides adjustment of the time interval between breaths for which no apneic event will be detected up to a maximum time of about 55 seconds. Resistor R46 sets the minimum time interval at approximately 5 seconds, assuming that resistor R45 has been set at its minimum point.

Upon detection of an apneic event, an audible alarm is immediately sounded by piezo alarm 73, seen in FIG. 6, provided that enabling switch 72, also seen in FIG. 6, is closed. Alarm 73 is driven at a frequency of approximately 2.4 kHz, by a square wave oscillator of a form well known to those skilled in the art, composed of amplifier 71, resistors R35, R36, and R37, and capacitors C9 and C10, as seen in FIG. 6. Most simply, amplifier 71 is the fourth, and heretofore unused amplifier, of the quad operational amplifier previously described. When pin 9 of timer 77 goes false, i.e., indicating an apneic event, amplifier 71 is gated into self-sustaining oscillation. Coupling capacitor C9 acts only to block the DC output of amplifier 71 when the oscillator circuitry is off, thus protecting piezo alarm 73, while transmitting the square-wave output of amplifier 71 to alarm 73 when the oscillating circuitry is activated. Detection means 70 may be reset and thus the audible alarm shut off by various means. Resumption of inspiratory effort reestablishes output true pulses from timer 41, pin 5, forcing the output of timer 77 pin 9 true, and normal operation resumes. Normally-open momentary switch 74, seen in FIG. 6, may be closed manually by the user, resetting detection means 70. Switch 72 may be opened by the user shutting off the audible alarm but without affecting the status of detection means 70.

The output of detection means 70, pin 9 of timer 77, is latched by an R-S flip-flop composed of resistors R38, R39, and R40, LED 75, and timer 77, pin connections 2, 4, 5, and 6 (exclusive of power supply connections), seen in FIG. 6. Assuming that pin 5 of timer 41 is false, upon detection of an apneic event, wherein pin 9 of timer 77 goes false, the above-described R-S flip-flop circuit is set and its output at pin 5 of timer 77 goes true, causing LED 75 to glow, thereby providing for a visible apnea alarm means. Resistor R40, as seen in FIG. 6, limits the current through LED 75 to approximately 14 mA. This visible alarm can only be manually shut off by opening switch 76 or by closing normally-open momentary switch 74.

The output states of timer 77 are subject to switching transients upon application of power, hence, some effort to establish consistent output states is desirable. Resistor-capacitor networks of resistor R39 and capacitor C11, and resistor R42 and capacitor C12, as seen in FIG. 6, hold pins 4 and 8 of timer 77, respectively, at ground potential L2, momentarily upon application of power, which prevents false triggering of both audible and visible alarms.

The present invention may be connected, using various electrical connecting means well known in the art, to a variety of display or recording devices so that information concerning the user's breathing pattern can be observed and studied. To provide for a proper connection such ancillary devices must have a sufficiently large input impedance or buffering to prevent loading of the circuitry of the present invention. All such breathing pattern information is based on the conditioned output of sensing means 20 available on line L11, as seen in FIG. 2, which line must be buffered by any external device to prevent alteration of the magnitude of the signal input at 33a to comparator 33. Provided that source 80 is connected as shown in FIG. 1, the voltage at line L11, referenced to ground potential L2, may be used to detect and record inspiratory and expiratory occurrences, with detection in a like manner to the device herein. This same electrical signal may be used to detect the flow of respirable gas through conduit 23 and nasal cannula 21, as seen in FIG. 1, since such flow of respirable gas produces a signal output at line L11 at negative saturation of amplifier 32, near the negative supply potential L3, due to pressurization of conduits 22 and 23 applied at pneumatic input 20a of sensing means 20. Should source 80 be disconnected and respirable gas no longer flow through conduit 23 and nasal cannula 21, line L11 may be used to display complete airway pressure for the entire inspiratory/expiratory cycle.

Inspiration detection comparator 33 output 33c may be interfaced directly to external devices provided that these devices have an input impedance of at least 10K ohms. This signal, available along line L6, is particularly valuable provided that source 80, seen in FIG. 1, is not connected and respirable gas is not flowing since, under these conditions, inspiration detection comparator 33, with the convention of inverse logic, remains true at the negative supply potential L3, for a time period coincident with the duration of inspiration and remains false (at the positive supply potential L1) for a time period coincident with the duration of expiration. This output may be recorded, displayed, counted, or may be used as control input to an inspiratory/expiratory (I/E ratio) time detector. The output available along line L6 may be used to detect, display or count inspiratory occurrences if source 80 (FIG. 1) is connected and respirable gas is permitted to flow provided that time delay circuitry as described previously is employed externally to suppress spurious inspiratory detection pulses as caused by depressurization of conduits 22 and 23 as seen in FIG. 1 and subsequent overshoot and ringing of sensing diaphragm of sensing means 20, or by continued inspiration of the user beyond the delivery period of electronic timing means 40.

Frequency-to-voltage converter amplifier 61 (FIG. 5) output 61c is available on line L12 provided that a high impedance buffer is used between line C12 and any external display or recording device used. This signal output provides an indication of respiration rate, the average DC output on line L12, referenced to ground potential L2, being directly proportional to breath rate. Switch 52 (FIG. 4) must be open to permit operation of F/V converter amplifier 61.

Apneic event detection means 70, as seen in FIG. 1, has an output available from output pin 9 of timer 77, as seen in FIG. 6, along line L13 which goes "false" in conventional logic terminology upon detection of an apneic event. This output may directly drive an external recorder, counter, timer, or other display means of larger than 10K ohm input impedance, provided that CMOS interfacing techniques and precautions, well known to those skilled in the art, are rigorously observed.

The suggested values for the resistance and capacitances for the circuits described in FIGS. 2 through 6 are as follows:

| RESISTANCES | CAPACITANCES |
|---|---|
| FIG. 2 | |
| R1 = 10K | C1 = 0.1 u |
| R2 = 100K | |
| R3 = 100K | |
| R4 = 20K | |
| R5 = 100K | |
| R6 = 100K | |
| R7 = 10K | |
| R8 = 160K | |
| R9 = 10K | |
| R10 = 100K | |
| R11 = 100K | |
| R12 = 10 | |
| FIG. 3 | |
| R13 = 10K | C2 = 0.01 u |
| R14 = 10K | C3 = 10 u |
| R15 = 100K | C4 = 0.01 u |
| R16 = 10K | C5 = 2.2 u |
| R17 = 1 M | |
| R18 = 56.2K | |
| R19 = 100K | |
| R20 = 100K | |
| FIG. 4 | |
| R21 = 10K | |
| R22 = 100K | |
| FIG. 5 | |
| R23 = 100K | C6 = 0.048 u |
| R24 = 1 M | C7 = 10 u |
| R25 = 140K | C8 = 10 u |
| R26 = 10K | |
| R27 = 100K | |
| R28 = 100K | |
| R29 = 27K | |
| R30 = 100K | |
| R31 = 100K | |
| R32 = 10 M | |
| R33 = 100K | |
| R34 = 10K | |
| FIG. 6 | |
| R35 = 100K | C9 = 0.01 u |
| R36 = 100K | C10 = 1500 p |
| R37 = 100K | C11 = 2.2 u |
| R38 = 10K | C12 = 2.2 u |
| R39 = 100K | C13 = 22 u |
| R40 = 470 | |
| R41 = 10K | |
| R42 = 100K | |
| R43 = 10K | |
| R44 = 10K | |
| R45 = 2 M | |
| R46 = 220K | |

While the invention has been particularly shown and described with reference to the preferred embodiments thereof, it will be understood by those skilled in the art that various alterations in form and detail of the electrical components described herein may be made without departing from the spirit and the scope of the invention.

What is claimed is:

1. A supplemental respiratory device that delivering a respirable gas to a user, on a demand basis, which comprises:
    (a) pressure sensing means for sensing changes in airway pressure, relative to atmospheric pressure, caused by the user's inspiration, and for producing a variable first electrical signal proportional in strength to the intensity of the pressure differential;
    (b) inspiration detection means, responsive to the first electrical signal for producing a second signal when said first signal passes a settable threshold;
    (c) electronic variable timing means, for initiating a timing cycle in response to the second signal, and for producing a third electrical signal for the duration of the timing cycle;
    (d) an inspiration frequency detection means receiving the third electrical signal and from the frequency thereof producing a fourth electrical signal, said fourth electrical signal communicated to the electronic variable timing means for controlling the duration of said third electrical signal such that the frequency and duration of the third electrical signal are inversely proportional to each other;
    (e) respirable gas delivery means responsive to the third electrical signal allowing the gas to flow to the user only so long as the delivery means is receiving the third electrical signal.

2. The supplemental respiratory device as defined in claim 1 wherein the inspiration frequency detection means further comprises:
    a sample and hold amplifier receiving the third electrical signal and sensing the starting thereof, said amplifier producing a fourth electrical signal inversely proportional to the rate of receipt of said third electrical signals, said fourth electrical signal communicated to the respirable gas delivery means terminating said third electrical signal.

3. The supplemental respiratory device as defined in claim 1, wherein the electronic variable timing means further includes, suppressing means for preventing the second signal from initiating a timing cycle before the gas delivery means depressurizes, and so that the timing cycle is not re-triggered before the user has stopped inhaling.

4. The supplemental respiratory device as defined in claim 3, which comprises: nasal cannula means, connected to the respirable gas delivery means by a first pneumatic conduit for delivery of the gas to the user, and the cannula means also connected to the pressure sensing means by a second pneumatic conduit for communication to the sensing means of the relative airway pressure changes caused by the user, and respirable gas source means, connected to the respirable gas delivery means, for supplying the gas delivered to the user.

5. The supplemental respiratory device as defined in claim 4, which comprises:
    apneic event detection means, connected to the electronic variable timing means, for determining if the user has stopped breathing by monitoring the time lapse between the end of each timing cycle and the beginning of each succeeding timing cycle and causing an alarm signal to occur if the time lapse exceeds a pre-set length of time.

6. The supplemental respiratory device as defined in claim 5, which comprises: electrical connecting means for connecting with monitoring means so that information concerning the user's respiratory cycle can be recorded.

7. The supplementary respiratory device as defined in claim 1 wherein the pressure sensing means comprises a diaphragm-type pressure transducer producing a continuous variable first electrical signal.

8. The supplemental respiratory device as defined in claim 7 wherein the suppressing means comprises electronic gating inhibiting the electronic variable timing means from cycling for settable time delay.

9. The supplemental respiratory device as defined in claim 1 wherein the pressure sensing means continuously communicates with the gas delivery means for producing the first electrical signal; whereby the magnitude of the first electrical signal is indicative of the gas flow from the gas delivery means.

* * * * *